United States Patent [19]
Kamb

[11] Patent Number: 5,807,679
[45] Date of Patent: Sep. 15, 1998

[54] ISLAND HOPPING—A METHOD TO SEQUENCE RAPIDLY VERY LARGE FRAGMENTS OF DNA

[75] Inventor: Alexander Kamb, Salt Lake City, Utah

[73] Assignee: Myriad Genetics, Inc., Salt Lake City, Utah

[21] Appl. No.: 499,333

[22] Filed: Jul. 7, 1995

[51] Int. Cl.$^6$ .............................. C12Q 1/68; C12Q 1/70; C12P 19/34; C07H 21/04

[52] U.S. Cl. ................................. 435/6; 435/5; 435/91.1; 435/91.2; 536/24.3; 536/24.32; 536/24.33

[58] Field of Search .................................. 435/6, 5, 91.1, 435/91.2; 536/24.3–24.33

[56] References Cited

U.S. PATENT DOCUMENTS 5,407,799  4/1995  Studier ......................................... 435/6

OTHER PUBLICATIONS

Sanger, F. et al. (1977). "DNA sequencing with chain–terminating inhibitors," *Proc. Natl. Acad. Sci. USA* 74:5463–5467.

Maxam, A.M. and Gilbert, W. (1977). "A new method for sequencing DNA," *Proc. Natl. Acad. Sci. USA* 74:560–564.

Smith, L.M. et al. (1986). "Fluorescence detection in automated DNA sequence analysis," *Nature* 321:674–679.

Hunkapiller, T. et al. (1991). "Large–Scale and Automated DNA Sequence Determination," *Science* 254:59–67.

Saiki, R.K. et al. (1988). "Primer–Directed Enzymatic Amplification of DNA with a Thermostable DNA Polymerase," *Science* 239: 487–491.

Mullis, K.B. and Faloona, F.A. (1987). "Specific Synthesis of DNA in Vitro via a polymerase–Catalyzed Chain Reaction," *Methods in Enzymology* 155:335–350.

Saiki, R.K. et al. (1985). "Enzymatic Amplification of β–Globin Genomic Sequences and Restriction Site Analysis for Diagnosis of Sickle Cell Anemia," *Science* 230:1350–1354.

*Primary Examiner*—Stephanie W. Zitomer
*Assistant Examiner*—Dianne Rees
*Attorney, Agent, or Firm*—Venable, Baetjer, Howard & Civiletti, LLP

[57] ABSTRACT

The present invention is a technique which allows one to determine rapidly the nucleic acid sequence of large fragments of nucleic acids such as the inserts obtained from YACs, BACs and Pls. This method uses an array of random primers matched pairwise in all combinations to amplify portions of the fragments to be sequenced. Some of these PCR reactions result in the formation of single bands of amplified DNA which are called islands. These islands are randomly scattered along the fragment of nucleic acid. These individual islands are sequenced, but this leaves major gaps in the complete sequence of DNA. A second round of PCR is performed in which the ends of the islands are used to design primers pointing away from the islands, these primers being matched pairwise in all combinations. This round of PCR again results in some of the reactions forming single bands of amplified nucleic acid. These bands connect the islands determined earlier. This automatically allows one to place the islands and connecting bands in order and to complete the sequencing of the gaps. Using this method obviates the necessity of subcloning portions of the fragment or slowly sequencing along the fragment in serial fashion and is therefore much more rapid and less labor intensive than previously used methods.

7 Claims, 1 Drawing Sheet

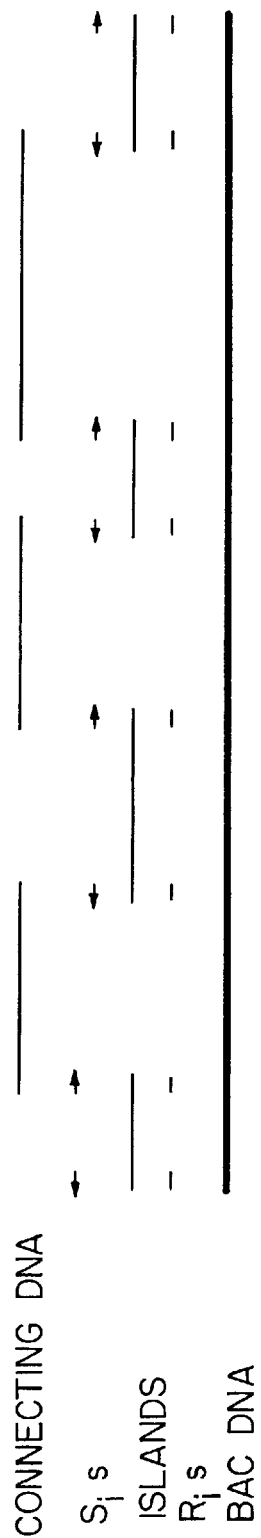

ISLAND HOPPING— A METHOD TO SEQUENCE RAPIDLY VERY LARGE FRAGMENTS OF DNA

BACKGROUND OF THE INVENTION

Genetic mapping and determination of DNA sequences has become of vital importance. Much effort is underway to sequence completely the genomes of model research organisms such as viruses, bacteria, yeast and the roundworm *C. elegans*. Much effort has already gone into preparing physical maps to be used for completely sequencing the human genome which is estimated to consist of 3 billion base pairs. Physical mapping and DNA sequencing is being used to locate genes associated with various diseases such as cancer, heart disease, etc. Because of the extremely large size of the human genome, this task has been somewhat daunting. The work is extremely labor intensive and therefore expensive. New techniques which decrease the labor involved are very desirable.

DNA sequencing methods were developed during the 1970s by Maxam and Gilbert (Maxam, A. M. and Gilbert, W., *Proc. Natl. Acad. Sci. USA* 74:560 (1977)) and by Sanger (Sanger, F., Nicklen, S. and Coulson, A. R., *Proc. Natl. Acad. Sci.* 74:5463 (1977)). During this time many other techniques now commonly used in molecular biology were also developed, e.g., cloning techniques, the development of vectors to be used in cloning, various blotting techniques, and eventually polymerase chain reaction (PCR) (see Innis, M. A. et al. (eds.) (1990), *PCR Protocols: A Guide to Methods and Applications* (Academic Press, San Diego, Calif.)) and other amplification schemes. Also during the 1970s it was discovered that genes are not found as single individual stretches of DNA along the chromosomes but rather very often the genes are split up into what are now called exons (regions of the gene which code for expressed sequences) and introns (regions of the gene which are intervening between the exons and which do not code for the final expressed product). Because of this intron-exon structure a single gene may, e.g., be split into more than 20 different segments (exons) and 5,000 bases of exon may be spread across 100,000 bases of chromosome sequence, the other 95,000 bases being introns. Therefore, if such a gene is found, to determine its base sequence will require sequencing 100,000 bases and not simply 5,000 bases. If one wants to sequence only the coding sequences, i.e., the exons, this can be done by preparing copies of the fully spliced messenger RNA (mRNA), these copies being called complementary DNA or cDNA. Nevertheless, it may be desirable to determine the sequence of the full gene, i.e., the full 100,000 bases because sequence in the introns may be important for proper splicing and expression of the gene. Mutations in the introns may thus be responsible for certain diseases.

In practice, when searching for specific genes, the complete genome is digested into smaller fragments which are inserted into vectors. These can vary dramatically in size depending on which vector is used. Plasmids such as pBR322 can carry inserts of only up to a few thousand bases. Putting the complete human genome into such a plasmid in pieces likely requires a library of at least 5 million distinct plasmid copies. The bacteriophage λ can carry inserts of 15–20 kilobases and therefore correspondingly fewer clones are required to hold the complete human library, but this still requires an extremely large number of separate clones which must be screened for the gene of interest. In more recent years newer vectors which can hold much larger inserts of DNA have been developed. These include cosmids, the yeast artificial chromosomes (YACs), bacterial artificial chromosomes (BACs) and P1s which are based on a double stranded bacteriophage. These can hold a wide range of insert sizes. P1 can accommodate inserts of approximately 85 kb, BACs hold inserts of about 150 kb, and YACs can have inserts ranging from a few hundred kb to a couple of thousand kb. With such libraries there are many fewer clones to be screened to find the gene of interest which saves much labor. Also, it is much more likely that the complete gene can be found within a single clone. Conversely, the resulting clone which is obtained contains much more DNA which must be analyzed.

When sequencing such large pieces of DNA containing 100–150 kb two methods have been used, primarily random shotgun sequencing and primer walking. One method was to purify the insert, cut it into much smaller pieces either by using enzymatic digestion or by random shearing, and subclone the smaller pieces into plasmids. A 100,000 bp fragment which is cut into fragments of roughly 2,000 bp requires 50 separate plasmids to hold all of the sequence. These 50 unique plasmids must be identified and sequenced. Even then one does not know how to arrange the fragments in their proper order. Usually, a second subcloning using a different enzyme digestion strategy is used. The resulting fragments are subcloned and sequenced and then the data analyzed against the first set of sequencing data to look for overlapping regions of sequence. In this manner the fragments can be placed in their proper order.

The second method traditionally used is simply to sequence the DNA in a serial fashion along the cloned piece of DNA. This is a very slow and laborious process. An individual sequencing reaction can determine the sequence of only about 300–700 bases. If one assumes an average sequencing run yielding data for 400 new nucleotides, to sequence 100,000 bases requires 250 separate sequencing reactions. Assuming one sequences in from both ends of the DNA, this requires 125 separate rounds of sequencing. For each round one needs to run a sequencing reaction, determine the sequence, and determine from this new data new primers for the next round of sequencing. Even if one can run one round of sequencing and prepare new primers in a single day, such a process requires 125 days of work to complete the sequencing. Such a serial technique is obviously impractical for sequencing such large pieces of DNA.

Newer methods utilizing parallel processing rather than the serial processing just outlined will greatly speed up the process of sequencing large fragments of DNA. A process which also automatically determines the proper ordering of smaller fragments cut from a larger fragment will also be an advance. The procedure of the present invention utilizes both of these advantages, i.e., it utilizes a parallel processing technique and also automatically determines the proper order of fragments. This technique can dramatically increase the rate of sequencing genes. The sequencing of the 3 billion base pairs of the human genome, as well as sequencing the genomes of other organisms, can be dramatically advanced by use of the present invention.

SUMMARY OF THE INVENTION

To sequence the complete genomes of several organisms requires the sequencing of vast amounts of DNA. The haploid human genome alone consists of approximately 3 billion base pairs. Even when searching for individual genes associated with a disease, one first narrows the location of the gene to a portion of a single chromosome, but then it is commonly required that hundreds of thousands of base pairs must be sequenced in completing the search for the gene. This sequencing is done without prior knowledge of any of the DNA sequence data. Multiple sequencing reactions must be done and for this it requires either determining sequence data so that new primers can be made to continue walking along the gene sequence or else the gene must be digested and subcloned into plasmids from which sequencing can be done directly using as primers pieces of DNA complementary to regions of the plasmid at the junction of the plasmid and the insert. The present invention utilizes a parallel processing technique rather than a serial processing technique to increase dramatically the rate at which these very large fragments of DNA can be completely sequenced. This new method also automatically determines the order of smaller fragments obtained from the large starting fragment. Furthermore, many steps of the present invention may be automated and there is minimal template preparation because the template is generated by PCR. Both of these facts further increase the rate at which data may be obtained.

The present invention takes advantage of combining in parallel the power of PCR techniques to increase dramatically the rate of completely sequencing very large fragments of DNA. The general technique is first to synthesize a pool of primers, called $R_i$s, consisting of either degenerate oligonucleotides which have unique sequences at their 5' ends and degenerate sequences at their 3' ends or else to use pools of individual primers of arbitrary sequences. In practice it is useful to use about 30 different primers. These primers are paired up in all possible combinations (other than with themselves) and used as primers for polymerase chain reactions. For 30 primers this will require 435 PCR reactions. Many of these pairings will result in no amplified DNA, some will produce several bands of DNA, and some portion will result in the production of single bands of amplified DNA. In practice it has been found that approximately 25% of the pairings produce single bands. The DNA formed in the reactions producing single bands of DNA is sequenced, the unique ends of the primers used in the PCR reaction being used as primers for the sequencing reactions. These sequenced bands will encompass only a portion of the total DNA desired to be sequenced. They will be randomly scattered along the full-length sequence with gaps between them. Because of this they are referred to as islands.

The sequence data obtained from the islands is used to prepare new primers, called $S_i$s, for another round of PCR which will "hop" between the islands. Primers complementary to the end regions of the islands and which point away from the islands, i.e., which will amplify away from the island rather than reamplifying through the island, are prepared. These can be mixed in all possible combinations of pairs and PCR performed using the complete large fragment as the template. It is preferable, however, to mix the $S_i$s in pools of 3 to decrease the total number of reactions. If 50 islands are originally identified then 100 new primers are prepared. By mixing the $S_i$s in pools of 3, a 33×33 grid can be prepared. This results in 528 pairings, excluding pairing a pool with itself. These, as well as the earlier, reactions are well suited to performing in microtiter plates and being handled by robotics. These PCR reactions are analyzed for the production of amplified DNA. In performing island hopping with pooled primers there is a small possibility that more than one amplified band may be seen from a single PCR. For example, if 50 islands had been found and 100 primers were synthesized to the ends of the islands and pooled in 33 groups of 3, there is about a 3% chance that any chosen primer will be matched with another primer to connect two islands, and about a 0.1% chance that two primer pairs in a single reaction will match up to connect two islands. Therefore roughly 1 in 1000 samples would produce 2 bands. Since 528 reactions would be performed there would be approximately a 50 % chance that there will be a single reaction which will show 2 distinct bands. If this is seen both bands are to be purified and sequenced. If 50 islands were identified it is expected that 49 of the pairings will result in the formation of amplified DNA. Those reactions so identified automatically order the islands and also these new bands are sequenced to fill in the sequence data between the islands. The use of automation, e.g., robotics and DNA synthesizers which can synthesize up to 48 primers overnight, allow for the processing of this many samples. Using such techniques fragments of 100–150 kilobases can very quickly be sequenced and the sequence data properly ordered. This process avoids the necessity of subcloning fragments or slowly sequencing the DNA in serial fashion.

Attention to certain variables and control experiments will further improve the procedure. The numbers of $R_i$s and $S_i$s may be varied. If an especially long stretch of DNA is to be sequenced it may be desirable to increase the number of $R_i$s. As control experiments, PCRs are run with the single primers. Often a single primer is found at both ends of an amplified DNA fragment. If the controls are performed, those reactions using single primers which result in single bands are compared to the PCRs in which those single primers are used as part of a pair of primers. If the identical sized band is produced from the pair of primers, such a band is to be considered spurious and not to be used. The use of such controls greatly decreases spurious data.

BRIEF DESCRIPTION OF THE DRAWING

The drawing shows the BAC insert DNA of 100 kilobases which is to be sequenced, the primers used for PCR, and the resulting amplified DNA fragments. The bottom line indicates the full-length DNA which is to be sequenced. Just above this are shown some of the printers, $R_i$s, used in the initial round of PCR, which result in amplified fragments of DNA being produced. The line above the $R_i$s indicates the islands which are produced from the initial round of PCR. The primers, $S_i$s, to be used in the second round of PCR are drawn just above the ends of the islands, the arrows indicating that these primers are designed to amplify sequence away from the islands and not through the islands. The top line indicates the connecting DNAs which result from the PCR reactions using $S_i$s as primers.

DESCRIPTION OF THE INVENTION

The present invention is directed to determining rapidly the complete sequence of large fragments of DNA. In general, the invention takes advantage of parallel processing of samples and a technique which results in the automatic ordering of subfragments of the DNA. The steps include polymerase chain reactions and ordinary DNA sequencing. More specifically, the method of the invention comprises: (a) isolating the DNA to be sequenced; (b) performing a first set of polymerase chain reactions using each possible pairing (other than pairing a primer with itself) of random primers, wherein each primer will work under reaction conditions which are the same for each primer; (c) analyzing each polymerase chain reaction of the first set of polymerase chain reactions and selecting reactions which produce single bands of DNA, wherein a first set of single bands of DNA referred to as islands is produced; (d) sequencing said island DNA produced in the first set of polymerase chain reactions to determine the island DNA sequence; (e) preparing a set of nonrandom primers corresponding to sequence from each end region of the islands wherein the primers of this second set point away from the islands; (f) performing a second set of polymerase chain reactions using each possible pairing of primers from the second set of primers; (g) analyzing each polymerase chain reaction of said second set of polymerase chain reactions and selecting reactions which produce single bands of DNA, wherein a second set of single bands of DNA referred to as connecting DNA is produced; (h) sequencing the connecting DNA to determine the DNA sequence of the connecting DNA; and, (i) analyzing the DNA sequence of the islands and the connecting DNA and arranging the sequences in order to give a complete DNA sequence of said large fragment of DNA.

The present invention is extremely well suited to robotics and other automation. It does not require subcloning steps thus further speeding up the overall process of obtaining sequence data. The use of robotics and automation and the elimination of subcloning greatly speed up the rate of sequencing of large fragments of DNA, something necessarily done in the search for genes associated with diseases and in the sequencing of complete genomes. This results in more rapid progress in the field of gene research and simultaneously lowers costs by eliminating much of the human labor which was previously required.

The present invention, referred to as "island hopping", takes advantage of the power of PCR. In brief the invention is as follows: A set of random primers, e.g., 30 primers each of unique sequence, each of 16 nucleotides, is prepared and the primers are combined in all possible pairs (excluding pairing a primer with itself). These primers are referred to as $R_i$s. The $R_i$s are designed to have nearly equivalent $T_m$s so that they will work equally efficiently under a single set of PCR conditions. Using a set of 30 primers results in 435 possible combinations. These combinations of primers are used as primer pairs for PCR using as the template the gene fragment to be sequenced. The vector containing the gene fragment is purified and subjected to PCR using each of the primer pairs. Low stringency conditions are used and the resulting "sloppiness" of PCR ensures that some fraction, often approximately 25% of the reactions, results in the production of single bands of amplified DNA as seen when a portion of each reaction is run on a gel. These bands of DNA are directly sequenced by standard techniques using the known sequences of the primer ends to prepare primers for the sequencing reactions. These bands of DNA represent small, separate portions of the large fragment and are referred to as "islands". The sequence data for the islands are analyzed to determine if any of the islands overlap.

The DNA between the islands (called "connecting DNA") is obtained by hopping between the islands. To do this, primers complementary to the end regions of the islands such that they will amplify away from the islands are designed and synthesized. These primers are called $S_i$s. If 50 islands had been found and sequenced then 100 primers, corresponding to the 100 ends of the 50 islands, are prepared. As was done with the $R_i$s, the $S_i$s are to be combined pairwise in all possible combinations or in pools of a defined size which can be combined pairwise and used in PCR reactions using the full-length large fragment as the template. Using 100 primers a total of up to 5,000 unique pairings is possible, although by combining the $S_i$s into pools the number of reactions to be performed will be much smaller than this. Again, a percentage of these will each result in the production of a single amplified fragment of DNA. It is expected that if n islands were found, the $S_i$s will result in n–1 amplified fragments which connect the n islands. These new fragments are sequenced directly by ordinary sequencing techniques such as the Sanger dideoxy method using fluorescent labels and run on a gel sequencer for automated sequence analysis. Primers for the sequencing reactions are known based on the primers used for the PCR reactions. Furthermore, since the combination of primers resulting in each band is known, and these were based on the sequences determined in the islands, one can automatically place the islands in their proper order along the gene. This greatly simplifies the overall process of sequencing and ordering the gene fragments.

A detailed description of the invention follows.

I. Island Sequence Production

A. Removal of Host Contamination

The DNA sequence to be determined will normally be contained in a vector obtained from a host organism. The vector is isolated from the host. A common example is to have the DNA of interest cloned into a BAC vector. For such a case, the complete, closed circular BAC DNA is isolated by any one of a number of well-known techniques. This purified DNA is resuspended in 10 mM Tris, 1 mM EDTA, pH 8 (TE buffer) at 100 ng/μl. Any $E.$ $coli$ contamination is removed as follows: mix 5 μl DNA (500 ng), 5 μl 10×plasmidsafe buffer (available from Epicenter), 7.5 μl 10 mM ATP, 5.0 μl plasmidsafe @ 250 units/μl (Epicenter), and 27.5 μl $H_2O$. Heat overnight at 37° C. then stop the reaction by heating at 75° C. for 10 minutes. The integrity of the plasmidsafe treated BAC DNA is then examined. This can be done by any of several methods, but the preferred method is a PCR dilution technique. A sample of the plasmidsafe treated BAC DNA as well as a sample of the BAC DNA saved from the step prior to treating with plasmidsafe are each used as templates in PCR reactions. Two sets of PCR are run with each sample. In one set the primers used are specific to BAC and in the other set the primers used are specific for $E.$ $coli$, e.g., $E.$ $coli$ 975-173.111F and $E.$ $coli$ 975-173.333R. A series of 10 fold dilutions is prepared for each set for running the PCR. Any standard PCR conditions can be used. These are widely known in the art. The integrity of the BAC DNA is determined by comparing the results of the samples from the before and after treatments with plasmidsafe relative to the integrity of $E.$ $coli$ contamination.

B. Primers for Arbitrary PCR

A set of 30 primers is prepared. These primers are matched so that they will work equally well or nearly equally well under the single set of PCR conditions to be used. For example, they may be designed so each has a predicted $T_m$ within a certain narrow range. The primers can be designed each to have a unique 5' sequence (which will later be used as the primer for sequencing reactions) and a degenerate 3' sequence or the primers may simply be individual primers of arbitrary sequence. Various lengths of primers can be designed, but it is preferable to use primers of lengths 13–30 nucleotides, more preferably primers of lengths 15–25 nucleotides, and most preferably primers of 15–20 nucleotides. Primers which are 16 nucleotides in length are most commonly used.

C. PCR

The polymerase chain reactions are performed as follows: Mix 1 μl of template DNA at 1 ng/μl, 2 μl of standard 10×PCR buffer (20 mM $MgCl_2$, 500 mM KCl, 100 mM Tris (pH 8.3) and 0.1% gelatin), 2 μl 2 mM dNTPs, 5 μl of primers at 1 μM, 0.25 μl Amplitaq polymerase, bring to 20 μl total with water. Either of the following two cycling conditions works well using a Perkin-Elmer Model 9600 thermocycler: 1) 1 cycle at 94° C. for 5 minutes followed by 40 cycles of 94° C. for 10 seconds, 42° C. for 10 seconds, and 72° C. for 30 seconds or 2) 1 cycle at 94° C. for 5 minutes, 4 cycles at 94° C. for 10 seconds, 38° C. for 10 seconds, and 72° C. for 30 seconds followed by 40 cycles at 94° C. for 10 seconds 50° C. for 10 seconds, and 72° C. for 30 seconds. The PCR reactions were prepared using an 8 probe Hamilton robot to set up an 8×8 matrix of pairs of primers using the program INI PCR in Eclipse software.

D. Purification of PCR Products

Only a fraction of the above PCR reactions results in production of amplified DNA fragments. There are many methods to analyze production of DNA fragments and to purify the amplified DNA. Here, the PCR reactions were ethanol precipitated, resuspended in TE buffer, and run on 0.8% agarose gels which were stained with ethidium bromide. Gel lanes which showed the amplified DNA had the cleanest looking bands excised from the gel by removing a plug of gel with a Pasteur pipet. The plug was resuspended in 100 μl water and heated at 95° C. for 10 minutes. This DNA was reamplified by removing 1 μl of the supernatant and using it as the template DNA for another PCR reaction, using as primers for each the same two primers which gave the original amplification of each DNA. The PCR reactions are performed as above, an aliquot of each reaction is run on a gel to quantify the result, and the remaining amplified portion is treated with 1 μl of exonuclease 1 and shrimp alkaline phosphatase at 37° C. for 30 minutes followed by 80° C. for 10 minutes. The resulting product can be purified as desired such as by phenol extraction and ethanol precipitation. These DNA fragments are referred to as "islands".

If the first round of PCR resulted in a high yield of DNA, it is possible to skip the gel purification and reamplification and simply to dilute the amplified DNA and use directly in the sequencing steps which follow.

E. Sequencing of the Islands

The island DNA is sequenced by any one of the many methods which are commercially available. Here sequencing was performed using the protocols for the ABI cycle sequencing. Fifty nanograms of DNA was used for each kilobase of DNA present in the island, e.g., if the island was 3 kb in length then 150 ng of DNA was used for the sequencing. The primers used for the sequencing correspond to the primers used for the PCR reactions. If the primers used for the PCR had unique 5 ' ends with degenerate 3 ' ends, the primers for the sequencing reactions corresponded to the unique portion of the PCR primers.

F. Analysis of the Islands

At this point some of the islands may in fact overlap in sequence. This can be the result of at least two possibilities. As one example, imagine 4 primers which lie in order along the total fragment to be sequenced. A PCR using primer pair 1 and 3 may have given a PCR product and also a PCR using primer pair 2 and 4 may have given a DNA product. These will overlap in the region between primers 2 and 3. Also, products may have been seen using primer pair 1 and 2 and also using primer pair 1 and 3. These will overlap between the primers 2 and 3. One can see that it becomes relatively easy to begin putting these islands in order, at least to the extent that there is overlap. There will almost certainly be regions of DNA which were not amplified by the above rounds of PCR. These gaps between islands must be filled in by further work which is referred to as "island hopping".

II. Island Hopping

After analyzing the sequence data of the islands and connecting as many islands as possible into the largest islands possible from this initial set of data, the ends of the islands are used to design new sets of primers to be used in PCR with the primers pointing away from the islands. In the example given above with primers 1, 2, 3 and 4, if each possible pairing results in amplified DNA, there will be six islands produced (there are six possible combinations of the primers). From these it will be possible to connect all 6 islands into a single large island because of the overlap. For performing island hopping, one will design primers only from the ends of this large island, i.e., primers in the region of the original primers 1 and 4. There is no sense in using primers from the middle of this large island, i.e., there is no sense in using primers from the region of 2 and 3. Once the number of island ends to be used to design primers has been minimized by assembling contiguous fragments, the new set of primers is designed together. One may have 50 distinct islands thus requiring the design and synthesis of 100 primers corresponding to regions near the 2 ends of each island. It is beneficial if all of these primers work equally well or nearly equally well under a single set of PCR conditions. By allowing a region near the ends of the islands to which the primers may be complementary and not simply preparing primers complementary to the extreme ends of the islands, it is usually possible to design all of the primers to have similar $T_m$ s spread over a narrow range of temperatures. A simple computer program can be designed to analyze the end regions of the islands and to design primers which will work equally under a single set of conditions. This can also be determined without a computer by analyzing the base compositions and lengths of the primers manually. These primers are then matched in all possible pairs or are pooled and the pools matched in all possible combinations, and PCR is performed. Since some of the gaps between islands may be fairly large, it is desirable to use PCR conditions which will allow for the synthesis of large fragments of DNA. The preferred conditions are to use Stratagene's TaqPlus conditions with their high salt buffer and 1–2 ng of template DNA. The PCR cycling conditions using the Perkin-Elmer Model 9600 are: 1 cycle at 95° C. for 5 minutes followed by 30 cycles at 96° C. for 30 seconds, 65° C. for 30 seconds, and 72° C. for 20 minutes. As before the resulting initial bands of amplified DNA can be reamplified in a second round of PCR. These resulting bands are then sequenced. As before, the use of robotics for setting up the PCR and sequencing reactions is very desirable because of the large number of reactions to be performed. This sequence data will fill in all of the gaps that had been present between the islands. Knowledge of the pair of primers used resulting in each amplified band of DNA automatically discloses neighboring islands, and the sequence data obtained here fills in between the islands. Thus the ordering of sequence is very easily determined.

The described procedure can be used to sequence rapidly very large fragments of DNA such as are commonly utilized for genome research. The initial part of the process takes advantage of the "sloppiness" of PCR to generate small islands of DNA which are sequenced. These are then used to generate new primers for a second round of PCR to fill in the gaps between the islands. The resulting amplified DNA fragments are sequenced thus filling in all of the sequence. The procedure leads to an automatic ordering of sequence data avoiding the necessity of doing different methods of subcloning and finding overlapping regions of the subcloned sequences. By avoiding the necessity of subcloning, and by doing parallel reactions, the complete process is dramatically speeded up. The process lends itself to the use of automation and computer programs to handle the large number of reactions and primer design which are necessary for the process. If desired, to decrease the number of samples, primers may be mixed in small pools rather than simply in pairs.

The exact methods used herein can be modified easily to suit one's preference. It is well known in the art that there are many variations possible for each step used, e.g., many ways of purifying DNA, many conditions used for PCR, several types of kits are available for DNA sequencing which all vary slightly in enzymes, buffers, temperatures, etc. which are to be used. The present invention is intended to include all of these minor variations which are well known in the art and are virtually equivalent with one another.

What is claimed is:

1. A method for rapidly sequencing large fragments of DNA, said method comprising the steps of:
   (a) isolating the DNA to be sequenced;
   (b) performing a first set of polymerase chain reactions using a set of random primers in each possible pairing of said random primers other than pairing a primer with itself, wherein each primer will work under reaction conditions which are the same for each primer;
   (c) analyzing each polymerase chain reaction of said first set of polymerase chain reactions by running an aliquot of each reaction on a gel and selecting reactions which produce a set of single bands of DNA on said gel, wherein said set of single bands of DNA is referred to as island DNA;
   (d) sequencing said island DNA to determine island DNA sequences;
   (e) preparing a set of nonrandom primers, each nonrandom primer being complementary to a portion of the nucleotide sequence from an end region of said island DNA, said end region comprising from 10–100 nucleotides, wherein said nonrandom primers bind to said island DNA such that the 3' end of said primer is at or near an end of said island DNA and the 5' end of said primer is farther from said end of said island DNA than is the 3' end of said primer;
   (f) performing a second set of polymerase chain reactions using each possible pairing of nonrandom primers;
   (g) analyzing each polymerase chain reaction of said second set of polymerase chain reactions by running an aliquot of each reaction of a gel and selecting reactions which produce amplified bands on said gel, wherein said amplified bands of DNA are referred to as connecting DNA;
   (h) sequencing said connecting DNA to determine connecting DNA sequences; and,
   (i) analyzing said island DNA sequences and said connecting DNA sequences and arranging all sequences in order to give a complete DNA sequence of said large fragment of DNA.

2. The method of claim 1 wherein said set of random primers consists of primers wherein all primers have an identical sequence of 10–50 nucleotides at their 5' ends and have a different, degenerate sequence of nucleotides in the remaining portion of the primer.

3. The method of claim 1 wherein robotics are used to perform the polymerase chain reactions.

4. The method of claim 1 wherein robotics are used to perform the DNA sequencing reactions.

5. The method of claim 1 wherein said nonrandom primers are designed with the aid of a computer program.

6. The method of claim 1 wherein nonrandom primers are used in pools of defined numbers of primers rather than being used in pairs.

7. The method of claim 6 wherein one or more of said second set of polymerase chain reactions results in production of more than a single band of connecting DNA.

* * * * *